United States Patent [19]

Bernhagen et al.

[11] 4,283,564

[45] Aug. 11, 1981

[54] PROCESS FOR PREPARING METHACROLEIN

[75] Inventors: Wolfgang Bernhagen, Mülheim; Hanswilhelm Bach, Duisburg; Eike Brundin, Dinslaken; Wilhelm Gick, Duisburg; Helmut Springer; Adolf Hack, both of Oberhausen, all of Fed. Rep. of Germany

[73] Assignee: Ruhrchemie AG, Oberhausen, Fed. Rep. of Germany

[21] Appl. No.: 106,211

[22] Filed: Dec. 21, 1979

[30] Foreign Application Priority Data

Dec. 22, 1978 [DE] Fed. Rep. of Germany ....... 2855504

[51] Int. Cl.$^3$ .............................................. C07C 47/22
[52] U.S. Cl. .................................................. 568/461
[58] Field of Search ................... 260/601 R; 568/463, 568/420, 433, 459, 463, 464

[56] References Cited

U.S. PATENT DOCUMENTS

| | | | |
|---|---|---|---|
| 2,518,416 | 8/1950 | Bortnick | 260/601 R |
| 2,639,295 | 5/1953 | Hagemeyer | 260/601 R |
| 2,848,499 | 8/1958 | MacLean et al. | 260/601 R |
| 3,463,818 | 8/1969 | Blumenthal | 260/601 R |

FOREIGN PATENT DOCUMENTS

225161 12/1968 U.S.S.R. ............................. 260/601 R

OTHER PUBLICATIONS

Taskashi "Chem. Abstracts" vol. 60, p. 2775 (Japan patent 23,159, Oct. 31, 1963, abst.).
Handbook of Chemistry and Physics, 55th ed. 1974–1975, pp. C-101 & C305.
Malinowski et al. "Chem. Abstract" vol. 56, pp. 2321g–2322a (1962).
Farberov et al. "Chem. Abstract" vol. 59, p. 393, p. 394 (1963).

*Primary Examiner*—Werren B. Lone
*Attorney, Agent, or Firm*—Sprung, Felfe, Horn, Lynch & Kramer

[57] ABSTRACT

A process for preparing methacrolein by catalytic reaction of propionaldehyde with formaldehyde is disclosed wherein the catalyst comprises a mixture of secondary amine and organic carboxylic acid with up to 8 carbon atoms.

14 Claims, No Drawings

PROCESS FOR PREPARING METHACROLEIN

BACKGROUND OF THE INVENTION

1. Field of the Invention

The invention relates to a new process for preparing methacrolein (2-methylpropenal) from propionaldehyde and formaldehyde.

2. Discussion of the Prior Art

Methacrolein is an important intermediate in the preparation of various organic compounds, in particular in the fields of perfumes and fragrances, pharmaceuticals, and polymers.

Numerous methods are already known for preparing methacrolein. Thus, for example, methacrolein can be obtained from isobutene by catalytic oxidation. The olefin is passed at 300° to 600° C. over suitable catalysts, in particular those containing vanadium, tungsten or molybdenum. The yields are between 40 and 80 percent referred to converted isobutylene. The use of high temperatures and sensitive catalysts raises a number of chemical engineering and technical problems that restrict the applicability of this method of preparation.

Reference may also be made to the preparation of methacrolein by oxidizing isobutyraldehyde on a catalyst containing molybdenum or uranium. (See French No. 13 40 385). The required reaction temperature is 275° C. to 375° C. The disadvantage of this process is the low yield, which is only about 25 percent.

A further group of processes for preparing methacrolein start from propionaldehyde and formaldehyde. One such process is based on the condensation of the starting aldehydes at 275° C. using catalysts containing sodium oxide and silicic acid. Methacrolein is obtained in a yield of about 46 percent by this process (sec. C.A. Vol. 56 (1962) 2321 and 2322).

Methacrolein can be prepared from propionaldehyde by means of a Mannich reaction, i.e., the condensation of ammonia or a primary or secondary amine, normally present as a salt, with formaldehyde and a compound containing a reactive hydrogen atom. Corresponding processes are described in C.A. Vol. 59 (1963), 393, 394, and also in U.S. Patent Specifications 144,164 and 2,848,499.

Despite the good methacrolein yields that can be obtained by the Mannich reaction, this process is not widely used industrially. A drawback is the necessity to use amines in stoichiometric amounts. In addition, the use of hydrochlorides, in which form the amines are generally employed, has considerable disadvantages. Thus, halogen-resistant apparatus must be used in order to prevent the occurrence of stress crack corrosion, which is a danger particularly when operating under elevated pressure.

Attempts have been made to circumvent these difficulties by carrying out the reaction between propionaldehyde and formaldehyde in the liquid phase using sulphuric acid or p-toluenesulphonic acid as catalysts (see Japanese No. 23 159). However, this reaction produces methacrolein in a yield of only about 60 percent.

To summarize, it may be said that the heretofore known processes for preparing methacrolein have considerable disadvantages, particularly as regards the low yields or difficulties experienced in the technical implementation.

It therefore became desirable to provide a process that avoids the afore-mentioned disadvantages and produces methacrolein in high yields without great technical expense or effort.

SUMMARY OF THE INVENTION

Broadly, this invention contemplates a process for preparing methacrolein by catalytic reaction between propionaldehyde and formaldehyde. The process is characterized in that a mixture of a secondary amine and an organic acid with up to 8 carbon atoms is used as a catalyst system.

An important feature of the process according to the invention is the use of a secondary amine in combination with an organic acid with up to 8 carbon atoms, as the condensation catalyst. In contrast to the Mannich reaction, this new process involves a catalyst conversion since the amine is used not in a molar ratio, but simply in catalytic amounts.

The formaldehyde and propionaldehyde can be used in stoichiometric amounts. It is however also possible to use an excess of formaldehyde, up to 1.5 moles of formaldehyde preferably being used per mole of propionaldehyde.

Formaldehyde is used either as an aqueous solution or as a polymer, for example, paraformaldehyde.

The use of a solvent is not essential, but is preferable when using a polymeric form of formaldehyde. Suitable solvents include 2-ethylhexanol, isododecane and toluene.

The catalyst system consists of a mixture of an organic acid with up to 8 carbon atoms and a secondary amine. Organic acids that have proved suitable include alkanoic acids, such as formic acid, acetic acid, propionic acid, n- or i-butanoic acid, oxalic acid, maleic acid, acetylene dicarboxylic acid, malonic acid, glutaric acid, succinic acid, tartaric acid, adipic acid, hydroxy succinic acid, salicylic acid and 2-ethylhexanoic acid. Mixtures of organic acids containing up to 8 carbon atoms can also be used. 0.002 to 0.05 mole of the acid is used per mole of propionaldehyde.

The second component of the catalyst system is a secondary amine, which is used in an amount of 0.005 to 0.1 mole per mole of propionaldehyde. Suitable secondary amines are $C_{1-8}$ secondary amines, e.g., dipropylamine, methylbutylamine, ethylbutylamine, di-2-ethylhexylamine, diphenylamine, dicyclohexylamine, diisooctylamine, piperidine, pyrrolidine, piperazine or morpholine has proved particularly suitable.

The conversion is normally carried out as a liquid phase reaction, maintaining a reaction pressure of between 2 an 10, preferably 2 and 4 atmospheres, although one can also carry out the conversion in the gas phase. The reaction temperature is between 70° and 120° C., preferably between 95 and 110° C.

When carrying out the conversion as a liquid phase reaction, the process is performed in a pressure vessel in which formaldehyde, propionaldehyde and the carboxylic acid are placed under a nitrogen atmosphere, followed by the fractional addition of the secondary amine, preferably while cooling and vigorously stirring. The reaction mixture is then heated to the conversion temperature and the reactants are allowed to react. The conversion is complete after about 30 to 120 minutes. The reaction mixture is cooled and is then separated into an organic phase and an aqueous phase. Methacrolein is obtained from the crude product by fractional distillation in a yield of more than 96 percent, referred to the propionaldehyde employed, and is obtained more than 99 percent pure. Additional purification is not necessary for most applications.

The process according to the invention enables methacrolein to be prepared at low temperatures and under conditions that do not require special apparatus. A noticeable feature is the high yield of pure methacrolein that is obtained despite the simple reaction procedure.

The process according to the invention is illustrated in the following example. EXAMPLE 104.4 kg of propionaldehyde, 2 kg of propionic acid and 198 kg of a 30 percent aqueous formaldehyde solution are mixed under a nitrogen atmosphere in a 0.6 m$^3$ capacity pressure vessel provided with a stirrer, and 5.8 kg of di-n-butylamine is added thereto within about 30 minutes and while cooling. The temperature in the pressure vessel rises to about 30° C. The reaction mixture is heated to 95° to 100° C. within 30 minutes, and a pressure of 2.5 atmospheres is established. The reaction is complete after about 60 minutes. The reaction mixture is cooled and then separated into an organic and an aqueous phase. The organic phase is found by gas chromatographic analysis to have the following composition (not taking into account water and formaldehyde):

Propionaldehyde—0.2%
Methacrolein—92.7%
Aldol—5.6%
Miscellaneous—1.5%

103 kg of methacrolein having a purity of more than 99.5 percent is obtained from this crude product by fractional distillation, which corresponds to a yield of 81.7 percent. Further methacrolein can be obtained from the aqueous phase by distillation.

What is claimed is:

1. In a process for preparing methacrolein by catalytic reaction between propionaldehyde and formaldehyde, the improvement wherein said catalyst is a mixture of a secondary amine and an organic carboxylic acid with up to 8 carbon atoms selected from the group consisting of formic acid, acetic acid, propionic acid, n-butanoic acid, i-butanoic acid, oxalic acid, maleic acid, acetylene dicarboxylic acid, malonic acid, glutaric acid, succinic acid, tartaric acid, adipic acid, hydroxy succinic acid, salicylic acid and 2-ethylhexanoic acid and the process is carried out at a temperature of 70° to 120° C.

2. A process according to claim 1 wherein the catalyst comprises 0.005 to 0.1 mole of a secondary amine and 0.002 to 0.05 mole of a carboxylic acid containing up to 8 carbon atoms, the molar amounts in each case referring to the amount of propionaldehyde used.

3. A process according to claim 1 wherein the reaction pressure is 2 to 10 atmospheres.

4. A process according to claim 1 wherein the reaction temperature is 95° to 110° C.

5. A process according to claim 3 wherein the reaction pressure is 2 to 4 atmospheres.

6. A process according to claim 1 wherein the secondary amine is a $C_{1-8}$ secondary amine.

7. A process according to claim 6 wherein said amine is di-n-butyl amine, dipropylamine, methylbutyl amine, ethylbutyl amine, di-2-ethylhexylamine, diphenylamine, dicyclohexylamine, piperidine, pyrolidine, piperazine or morpholine.

8. A process according to claim 1 wherein the process is conducted in the liquid phase.

9. Process according to claim 1 wherein the reaction temperature is 70° to 110° C.

10. Process according to claim 9 wherein the process is conducted in the liquid phase.

11. Process according to claim 9 wherein the process is conducted in the gas phase.

12. Process according to claim 9 wherein the process is carried out in the presence of a solvent.

13. Process according to claim 12 wherein said solvent is selected from the group consisting of 2-ethylhexanol, isododecane and toluene.

14. Process according to claim 9 wherein the process is carried out at a pressure of 2 to 10 atmospheres, the catalyst comprises 0.005 to 0.1 mol of the secondary amine and 0.002 to 0.05 mol of a carboxylic acid selected from the group consisting of formic acid, acetic acid, propionic acid, n- or i-butanoic acid, maleic acid, oxalic acid, acetylene dicarboxylic acid, malonic acid, glutaric acid, succinic acid, tartaric acid, adipic acid, hydroxy succinic acid, salicyclic acid and 2-ethylhexanoic acid, the molar amounts in each case referring to the amount of propionaldehyde used.

* * * * *